United States Patent
Wang et al.

(10) Patent No.: US 10,188,501 B2
(45) Date of Patent: Jan. 29, 2019

(54) FORK-TYPE COVERED STENT

(71) Applicant: Lifetech Scientific (Shenzhen) Co., Ltd., Shenzhen (CN)

(72) Inventors: Yongsheng Wang, Shenzhen (CN); Caiping Liu, Shenzhen (CN); Deyuan Zhang, Shenzhen (CN); Wei Guo, Shenzhen (CN)

(73) Assignee: Lifetech Scientific (Shenzhen) Co., Ltd., Shenzhen (CN)

( * ) Notice: Subject to any disclaimer, the term of this patent is extended or adjusted under 35 U.S.C. 154(b) by 0 days.

(21) Appl. No.: 15/320,901

(22) PCT Filed: Jun. 19, 2015

(86) PCT No.: PCT/CN2015/081893
§ 371 (c)(1),
(2) Date: Dec. 21, 2016

(87) PCT Pub. No.: WO2015/196948
PCT Pub. Date: Dec. 30, 2015

(65) Prior Publication Data
US 2017/0128189 A1   May 11, 2017

(30) Foreign Application Priority Data
Jun. 27, 2014   (CN) .......................... 2014 1 0302282

(51) Int. Cl.
*A61F 2/07* (2013.01)
*A61F 2/06* (2013.01)
(Continued)

(52) U.S. Cl.
CPC .................. *A61F 2/07* (2013.01); *A61F 2/06* (2013.01); *A61F 2/856* (2013.01); *A61F 2/915* (2013.01);
(Continued)

(58) Field of Classification Search
CPC ...... A61F 2/06; A61F 2002/065; A61F 2/856; A61F 2002/067; A61F 2/954; A61F 2/07;
(Continued)

(56) References Cited

U.S. PATENT DOCUMENTS 6,030,414 A * 2/2000 Taheri .................. A61F 2/07
 623/1.1
6,033,435 A * 3/2000 Penn .................. A61F 2/856
 623/1.15
(Continued)

FOREIGN PATENT DOCUMENTS

CN         201046170 Y      4/2008
CN         101259045 A      9/2008
(Continued)

OTHER PUBLICATIONS

International Search Report dated Sep. 8, 2015 for PCT/CN2015/081893.

*Primary Examiner* — Alvin Stewart
(74) *Attorney, Agent, or Firm* — Raymond Sun (57) ABSTRACT

A bifurcated stem graft (10) comprises a body (100) and a side branch (200) that forms an acute angle with the body (100). The side branch (200) comprises a covering film (220) and a first bare stent (240) only disposed on the covering film (220). Part of the first bare stent (240) is positioned adjacent a boundary line (230) of the body (100) and the covering film (220) and is located in a vertex angle area (250) of the acute angle. Due to the fact that part of the first bare stem (240) is attached to the vertex angle area (250), after the stem (10) is released, the self-expanded part of the first bare stent (240) enables the vertex angle area (250) of the side branch (200) to be effectively supported, the covering film is not prone to shrinkage, and a leading wire can enter easily. Meanwhile, a special bare stent attached to the vertex angle area (250) does not need to be additionally disposed on the first bare stent (240), and thus the technology for preparing the bare stem is simplified; furthermore, the first bare stent (240) is only disposed on the side branch (200) and does not need to span the connecting (Continued)

part of the body (100) and the side branch (200), and thus the waveform can be shaped easily.

19 Claims, 11 Drawing Sheets

(51) Int. Cl.
   *A61F 2/856* (2013.01)
   *A61F 2/915* (2013.01)
   *A61F 2/82* (2013.01)
   *A61F 2/89* (2013.01)

(52) U.S. Cl.
   CPC ............ *A61F 2/89* (2013.01); *A61F 2002/061* (2013.01); *A61F 2002/065* (2013.01); *A61F 2002/075* (2013.01); *A61F 2002/828* (2013.01); *A61F 2230/0054* (2013.01)

(58) Field of Classification Search
   CPC ...... A61F 2/915; A61F 2/89; A61F 2002/061; A61F 2002/075; A61F 2002/828
   See application file for complete search history.

(56) References Cited

U.S. PATENT DOCUMENTS

| | | | | |
|---|---|---|---|---|
| 6,048,361 | A * | 4/2000 | Von Oepen | A61F 2/856 606/108 |
| 6,059,824 | A * | 5/2000 | Taheri | A61F 2/856 623/1.15 |
| 6,086,611 | A * | 7/2000 | Duffy | A61F 2/82 623/1.35 |
| 6,210,429 | B1 * | 4/2001 | Vardi | A61F 2/856 606/153 |
| 6,325,826 | B1 * | 12/2001 | Vardi | A61F 2/82 623/1.15 |
| 6,520,988 | B1 * | 2/2003 | Colombo | A61F 2/856 623/1.11 |
| 6,599,316 | B2 * | 7/2003 | Vardi | A61F 2/82 623/1.15 |
| 6,645,242 | B1 * | 11/2003 | Quinn | A61F 2/07 623/1.13 |
| 7,220,275 | B2 * | 5/2007 | Davidson | A61F 2/82 623/1.35 |
| 7,731,741 | B2 * | 6/2010 | Eidenschink | A61F 2/07 623/1.11 |
| 7,828,837 | B2 * | 11/2010 | Khoury | A61F 2/07 623/1.16 |
| 8,052,741 | B2 * | 11/2011 | Bruszewski | A61F 2/064 606/153 |
| 8,556,961 | B2 * | 10/2013 | Quinn | A61F 2/07 623/1.13 |
| 8,808,358 | B2 * | 8/2014 | Khoury | A61F 2/07 623/1.35 |
| 9,095,421 | B2 * | 8/2015 | Peterson | A61F 2/07 |
| 9,808,334 | B2 * | 11/2017 | Roeder | A61F 2/07 |
| 9,861,505 | B2 * | 1/2018 | Khoury | A61F 2/856 |
| 2002/0156517 | A1 * | 10/2002 | Perouse | A61F 2/064 623/1.11 |
| 2003/0125802 | A1 * | 7/2003 | Callol | A61F 2/856 623/1.35 |
| 2003/0195606 | A1 * | 10/2003 | Davidson | A61F 2/82 623/1.11 |
| 2004/0088007 | A1 * | 5/2004 | Eidenschink | A61F 2/856 607/1 |
| 2004/0117003 | A1 * | 6/2004 | Ouriel | A61F 2/07 623/1.35 |
| 2004/0138737 | A1 * | 7/2004 | Davidson | A61F 2/82 623/1.35 |
| 2005/0102023 | A1 * | 5/2005 | Yadin | A61F 2/856 623/1.15 |
| 2006/0136046 | A1 * | 6/2006 | Hartley | A61F 2/07 623/1.35 |
| 2006/0155362 | A1 * | 7/2006 | Israel | A61F 2/856 623/1.15 |
| 2006/0271160 | A1 * | 11/2006 | Gregorich | A61F 2/856 623/1.15 |
| 2006/0271161 | A1 * | 11/2006 | Meyer | A61F 2/856 623/1.15 |
| 2006/0287704 | A1 * | 12/2006 | Hartley | A61F 2/07 623/1.13 |
| 2007/0055356 | A1 * | 3/2007 | Eidenschink | A61F 2/07 623/1.25 |
| 2007/0067023 | A1 * | 3/2007 | Kveen | A61F 2/856 623/1.35 |
| 2007/0135903 | A1 * | 6/2007 | Gregorich | A61F 2/856 623/1.35 |
| 2007/0142904 | A1 * | 6/2007 | Sorenson | A61F 2/856 623/1.35 |
| 2007/0191922 | A1 * | 8/2007 | Hartley | A61F 2/07 623/1.2 |
| 2007/0208411 | A1 * | 9/2007 | Meyer | A61F 2/856 623/1.15 |
| 2007/0208414 | A1 * | 9/2007 | Sorenson | A61F 2/82 623/1.16 |
| 2007/0208415 | A1 * | 9/2007 | Grotheim | A61F 2/856 623/1.16 |
| 2007/0208418 | A1 * | 9/2007 | Hegg | A61F 2/856 623/1.35 |
| 2007/0208419 | A1 * | 9/2007 | Meyer | A61F 2/856 623/1.35 |
| 2007/0260304 | A1 * | 11/2007 | Gregorich | A61F 2/856 623/1.35 |
| 2007/0299505 | A1 * | 12/2007 | Gregorich | A61F 2/856 623/1.15 |
| 2008/0027533 | A1 * | 1/2008 | Oepen | A61F 2/856 623/1.35 |
| 2008/0114437 | A1 * | 5/2008 | Ozhered | A61F 2/856 623/1.11 |
| 2009/0043377 | A1 * | 2/2009 | Greenberg | A61F 2/07 623/1.35 |
| 2009/0138075 | A1 * | 5/2009 | Gregorich | A61F 2/856 623/1.42 |
| 2009/0259293 | A1 * | 10/2009 | Moloney | A61F 2/856 623/1.16 |
| 2009/0299460 | A1 * | 12/2009 | Meyer | A61F 2/856 623/1.12 |
| 2009/0319022 | A1 * | 12/2009 | Hartley | A61F 2/07 623/1.13 |
| 2011/0257731 | A1 * | 10/2011 | Hartley | A61F 2/07 623/1.35 |
| 2012/0046728 | A1 * | 2/2012 | Huser | A61F 2/07 623/1.13 |
| 2012/0290068 | A1 * | 11/2012 | Roeder | A61F 2/07 623/1.13 |
| 2013/0211505 | A1 * | 8/2013 | Robison | A61F 2/07 623/1.35 |
| 2014/0180393 | A1 * | 6/2014 | Roeder | A61F 2/07 623/1.15 |
| 2014/0371838 | A1 * | 12/2014 | Buddery | A61F 2/07 623/1.11 |
| 2015/0250626 | A1 * | 9/2015 | Fischer | A61F 2/07 623/1.13 |
| 2016/0184115 | A1 * | 6/2016 | Ondersma | A61F 2/856 623/1.35 |
| 2017/0007392 | A1 * | 1/2017 | Louren O | A61F 2/07 |
| 2017/0112642 | A1 * | 4/2017 | Hartley | A61F 2/856 |

FOREIGN PATENT DOCUMENTS

| | | |
|---|---|---|
| CN | 104116577 A | 10/2014 |
| CN | 203988497 U | 12/2014 |

* cited by examiner

FORK-TYPE COVERED STENT

TECHNICAL FIELD

The present invention relates to the technical field of medical devices, particularly to a bifurcated stent graft.

BACKGROUND

Aneurysm is a permanent limitation expansion of the blood vessel and it is called an aneurysm when the vessel diameter is increased by more than 50% of its normal size, If an aneurysm is in the abdominal aorta, an abdominal aortic aneurysm is formed. Iliac aneurysm is usually defined as the case that the local extension of the iliac artery diameter exceeds 1.5 cm. The iliac aneurysm is divided into isolated iliac aneurysm (see FIG. 1), independent iliac aneurysm (see FIG. 2), and iliac aneurysm accompanied by abdominal aortic aneurism (see FIG. 3). In 75% of the cases, iliac aneurysm is associated with abdominal artery. There are about 7.5% of the cases being isolated iliac aneurysm. The remaining aneurysm is the independent iliac aneurysm. In the United States, about 15,000 people die of abdominal aortic aneurysm (abdominal aortic aneurysm, AAA) rupture each year. It was believed in early reports that the iliac aneurysm having a diameter of more than 3 cm was fatal and it is recommended to be treated by surgery. Although this disease is thought to involve only 2% of the general population. it tends to occur in the elderly, and with the arrival of China's aging population, its incidence is rising.

Figure 1:
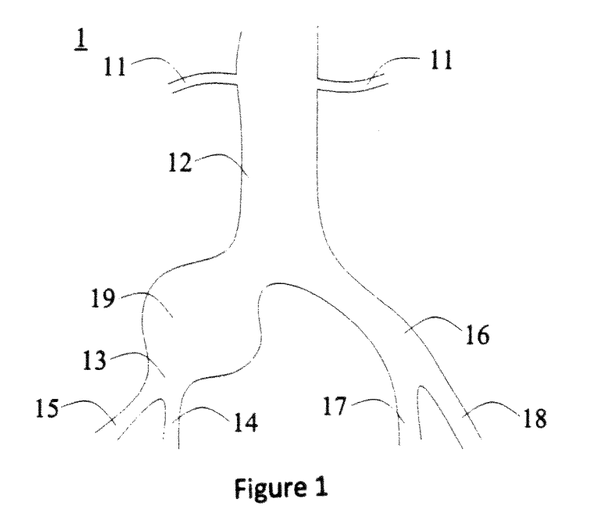
FIG. 1 is a schematic view of an isolated iliac artery aneurysm.
Figure 2:
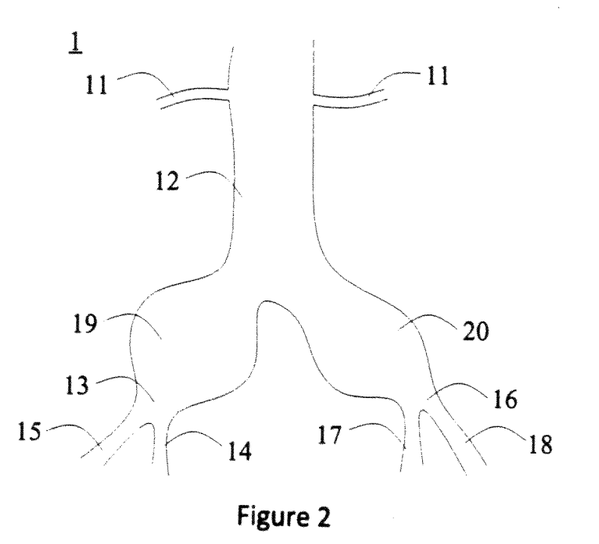
FIG. 2 is a schematic view of an independent iliac artery aneurysm.
Figure 3:
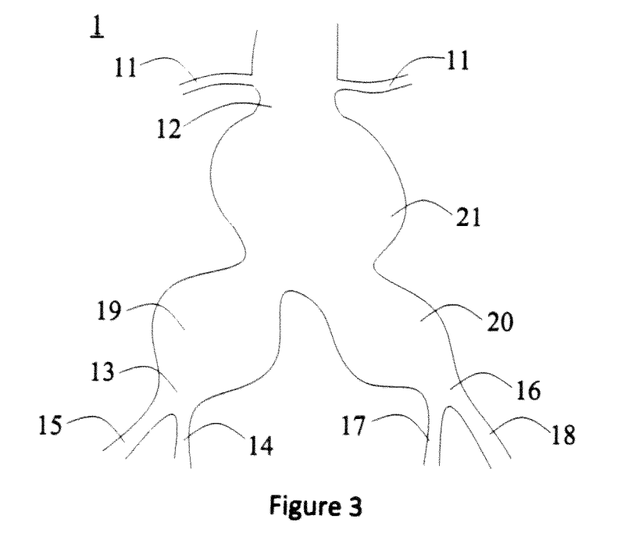
FIG. 3 is a schematic view of an iliac artery aneurysm accompanied with abdominal arterial aneurysm.

As shown in FIG. 1 to FIG. 3, the abdominal iliac artery 1 includes the renal artery 11 on the abdominal aorta, the abdominal aorta 12, the right arteria iliaca communis 13, the right internal iliac artery 14, the right external iliac artery 15, the left arteria iliaca communis 16, the left internal iliac artery 17 and the left external iliac artery 18. The protein degradation of connective tissues in arterial walls, inflammation and immune responses, as well as other factors, result in the loss of elastin in the middle and outer membranes, which causes the extension of tumors. Single iliac aneurysm, being not accompanied by abdominal aortic aneurysm, is known as an isolated iliac aneurysm, such as the right iliac aneurysm 19 as shown in FIG. 1. Several iliac aneurysms, being not accompanied by abdominal aortic aneurysm, are known as independent iliac aneurysm, such as the right iliac aneurysm 19 and the left iliac aneurysm 20 as shown in FIG. 2. Aneurysms existing in abdominal aorta and iliac artery are called iliac aneurysms accompanied by abdominal aneurysm, such as the right iliac aneurysm 19, the left iliac aneurysm 20 and abdominal aortic aneursm 21 as shown in FIG. 3.

Either open surgery or endovascular surgery can be used to repair the iliac aneurysms. Open repair can be carried out on all iliac aneurysms under anatomical conditions to replace arterial segments having pathological changes with artificial blood vessels, with good long-term results; however, the complications and mortality of iliac aneurysm open repair are equivalent to those of a major vascular surgery.

In the minimally invasive interventional treatment techniques which make use of endovascular exclusion principle, a covered stem is usually adopted to cover the aneurysm. At present, the commercially available covered stem is mainly composed of wire and PET (polyethylene terephthalate resin) membrane or ePTFE (polytetrafluoroethylene) membrane covered thereon, and the metal stent is made into a cylindrical or bifurcated metal frame. The compressed covered stent is delivered to the location of pathological changes and accurately released by a delivery system, and with the help of a developing system to cover the aneurysm, the stent isolates pathological changes and forms a new blood flow channel so that the aneurysm and arterial pressure are isolated, and the blood remaining in the lumen of the aneurysm gradually forms thrombosis and vascular tissue by muscularization. The expanded aneurysm wall contracts due to the negative pressure, thereby eliminating the hidden risks of tumor rupture and bleeding so as to achieve the purpose of healing.

In comparison, at present, endovascular repair is adopted to treat iliac aneurysms, which can only block the bilateral internal iliac arteries or unilateral internal iliac artery, which may cause complications such as impotence, gluteus claudication and pelvic ischemic. Many clinical research data show that retaining at least one side of the internal iliac artery can significantly reduce the incidence of above-mentioned complications. At present, it has been reported in the literature that the internal iliac bifurcated stent in the treatment of iliac aneurysms can open the bilateral internal iliac arteries and significantly reduce or avoid complications caused by the internal iliac artery blocking, which has distinct advantages.

The proximal end and distal end of the stent can be defined by the blood flow, which flows from the proximal end to the distal end of the stent.

Currently, the covered stent used for interventional treatment in the lumen of the iliac communis aneurysm affecting the internal iliac artery mainly consists of two types, respectively a straight-tube type covered stent and a bifurcated stent graft, wherein the straight-tube type graft stent further includes two types, including one with a horn mouth at the distal end and the other one without a horn mouth at the distal end. The straight-tube type stent has a proximal end and a distal end. A bifurcated stent means that the stent has a proximal end of the body and two distal ends of the branch.

When the straight-tube type covered stent without a horn mouth at the distal end is adopted, the distal end of the stent must be released in the external iliac artery in order to ensure that the distal end of the stem has a reliable anchoring and that no endo-leak will occur. Thus, the covered stent will block the internal iliac artery, which will result in pelvic ischemia, thereby causing the occurrence of complications such as gluteus claudication, colon ischemia, spinal cord ischemia, perineum necrosis and sexual dysfunction, When the straight-tube type covered stent with a horn mouth at the distal end is adopted, the distal end of the stent may be released approximate to the opening of the internal iliac artery and the stent with a horn mouth at the distal end is attached to the arteria iliaca communis wall. Thus, circulation of the internal iliac artery can be ensured; however, the stem does not completely isolate the arteria iliaca communis, which still carries the risk of rupture.

The bifurcated stem graft is composed of a body, a main branch and a side branch part. The body and the side branch are released in the arteria iliaca communis, with the distal end of the side branch being approximate to the internal iliac artery and the distal end of the main branch is released within the external iliac artery involved by no aneurysm. After the bifurcated stent graft has been completely released, an outer periphery covered stem is released into the internal iliac artery via the side branch and connected to the side branch. This ensures the circulation of the internal iliac artery and the complete isolation of the arteria iliaca communis. In summary, the bifurcated stent graft is a preferred option for the treatment of the arteria iliaca communis involving internal iliac artery. A common bifurcated stent graft comprises a body and a side branch, and an independent waveform ring is used to extend across the connection part of the body and the side branch of the stem, and surround a circle. However, because of irregular shape at the boundary between the body and the side branch, the independent waveform ring is hard to set, and the axial origination site of the side branch is not fully attached with the waveform ring, so that the side branch has insufficient radial support force at this site, resulting problems such as the covering film being likely to retract due to insufficient support force at this site, and difficulties for the guidewire to enter the side branch through the body.

SUMMARY OF THE INVENTION

Based on the above, there is a need to provide a bifurcated stent graft to address the problems that the support force at the boundary between the body and the side branch is insufficient, and that it is difficult for the guidewire to enter.

A bifurcated stem graft comprises a body and a side branch that forms an acute angle with the body, the side branch comprising a covering film and a first bare stent disposed only on the covering film, a part of the first bare stent is positioned adjacent the boundary between the body and the covering film, and is located in the vertex angle area of the acute angle.

In one of the embodiments, the first bare stent comprises a plurality of proximal vertices and distal vertices, the connection lines of the plurality of distal vertices are annular, and at least a part of the plurality of proximal vertices is located in the vertex angle area.

In one of the embodiments, the first bare stem comprises a plurality of proximal vertices and distal vertices, the connection lines of the plurality of distal vertices are along the same circumference, and at least a part of the plurality of proximal vertices is located in the vertex angle area.

In one of the embodiments, the plurality distal vertices is aligned with the distal end portion of the covering film.

In one of the embodiments, the body comprises a second bare stent positioned adjacent the boundary line, the second bare stent comprising two end support bars disposed at the opposite sides of the side branch, and the two end support bars are parallel to each other or symmetrical relative to the side branch.

In one of the embodiments, the tails of the end support bars are substantially smoothly rounded.

In one of the embodiments, the first bare stent is structured as a waveform open loop, the side branch also comprises a third bare stent disposed on the covering film, and the third bate stem is structured as a waveform close loop and connected with the first bare stent.

In one of the embodiments, the body comprises a second bare stent positioned adjacent the boundary, the second bare stent comprising two end support bars disposed at the opposite sides of the side branch, and the two end support bars are parallel to each other or symmetrical relative to the side branch.

In one of the embodiments, the tails of the end support bars are substantially smoothly rounded. In the above bifurcated stent graft, since the included angle between the body and the side branch is an acute angle, the covering film is retracted because the vertex angle area of the side branch is not supported by the bare stent, which not only results in the narrowing of the blood flow channel but also prevents the smooth entrance of the guidewire. In this application, a part of the first bare stent is attached to the vertex angle area, after the stent is released, the self-expanded part of the first bare stem can effectively support the vertex angle area of the side branch, so as to avoid the retraction of the covering film and facilitate the entrance of the guidewire. Meanwhile, there is no need for an additional bare stent to attach to the vertex angle area on the basis of the first bare stent, thus the technology for preparing the bare stent is simplified, and the first bare stent is disposed only on the side branch without going across the connection part of the body and the side branch, thus facilitating the waveform setting.

DETAILED DESCRIPTION OF THE INVENTION

In order to fully understand the invention, the bifurcated stent graft will now be described more fully with reference to the related drawings. Preferred embodiments of the bifurcated stent grafts are shown in the drawings. However, the bifurcated stent graft can be achieved in many different ways and is not limited to the embodiments described herein. Conversely, these embodiments are provided so that this disclosure of the bifurcated stent graft will be more thorough and complete.

It will be understood that when an element is referred to as being "fixed on" another element, it can be directly on the other element or intervening elements may also be present. When an element is referred to as being "connected with" another element, it can be directly connected with the other element or intervening elements may also be present. The terms "vertical", "horizontal", "left", "right" and the like are used herein for the purpose of explanation only and not intended to represent the only examples that can be practiced.

Unless otherwise defined, all technical and scientific terms used herein have the same meaning as commonly understood by those skilled in the art to which this invention belongs. The terms used in the description of the bifurcated stent graft herein arc for the purpose of describing particular examples only and are not intended to limit the invention. As used herein, the term "and or" includes any and all combinations of one or more of the associated listed items.

Figure 4:
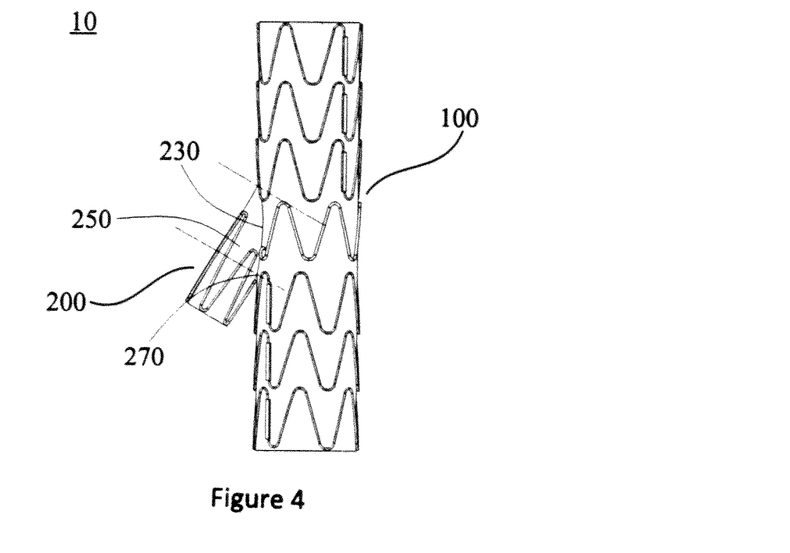
FIG. 4 is a schematic view of one embodiment of a bifurcated stent graft.

As shown in FIG. 4, the bifurcated stem graft 10 of one embodiment (hereinafter simply referred to as stent 10) comprises a body 100 and a side branch 200 that forms an acute angle with the body 100. The side branch 200 comprises a covering film 220 and a first bare stent 240 disposed only on the covering film 220. Part of the first bare stent 240 is approximate to a boundary line 230 of the body 100 and the covering film 220, and is located in a vertex angle area 250 of the acute angle.

The boundary line 230 is the borderline connecting the body 100 and the covering film 220; the vertex angle area 250 is a part of the side branch 200, as shown by the portion of the dashed lines in FIG. 4. The vertex angle area 250 is curved; the curve is formed by surrounding the boundary line 230 between the body 100 and the covering film 220 and the round section of the distal vertexes 270 through an acute angle; the round section preferably is parallel to the distal end of the side branch 200. In one embodiment, the first bare stein 240 is attached to the covering film 220 by means of suturing or glue. The stern 10 has two states, a compressed state and an expanded state; the compressed stent 10 is constrained to the sheath of the delivery apparatus for delivery in blood vessels. Each bare stem on each covering film is released in a self-expanding manner after delivery at the target place, with the diameter of stent 10 being slightly larger than that of the vessel, so that stent 10 can be closely attached to the vascular wall to form a new blood flow channel.

As the included angle between the body 100 and the side branch 200 is an acute angle, when no bare stent supports the side branch 200 from inside approximate to the boundary line 230 proximally connecting them (i.e. the vertex angle area 250), the covering film 220 will experience shortening, which not only results in the narrowing of the blood flow channel, but also prevents the smooth entry of the guidewire. In this invention, due to the fact that part of the first bare stent 240 is attached to the vertex angle area 250, after the stent 10 is released, the self-expanded part of the first bare stem 240 can effectively support the vertex angle area 250 of the side branch 200, so as to avoid the retraction of the covering film 240 and facilitate the entry of the guidewire. Meanwhile, a special bare stent attached to the vertex angle area 250 does not need to be additionally disposed on the first bare stent 240, and thus the technology for preparing the bare stent is simplified; furthermore, the first bare stent 240 is disposed only on the side branch 200 without extending across the connecting part of the body 100 and the side branch 200, thereby facilitating the waveform setting.

Figure 5:
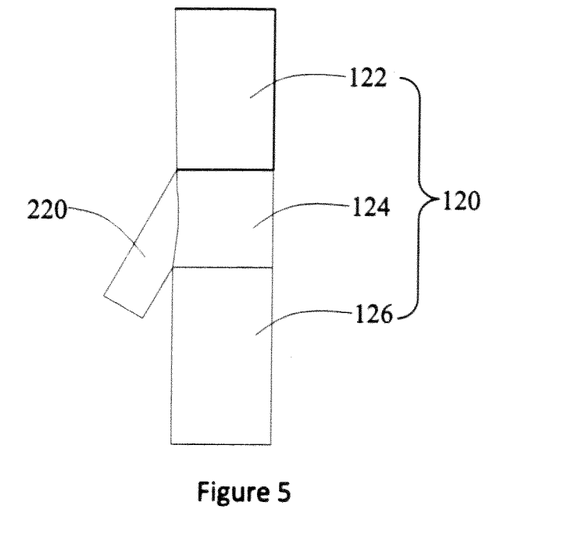
FIG. 5 is a schematic view of a covering film of the bifurcated stent graft and a body covering film of FIG. 4.
Figure 6:
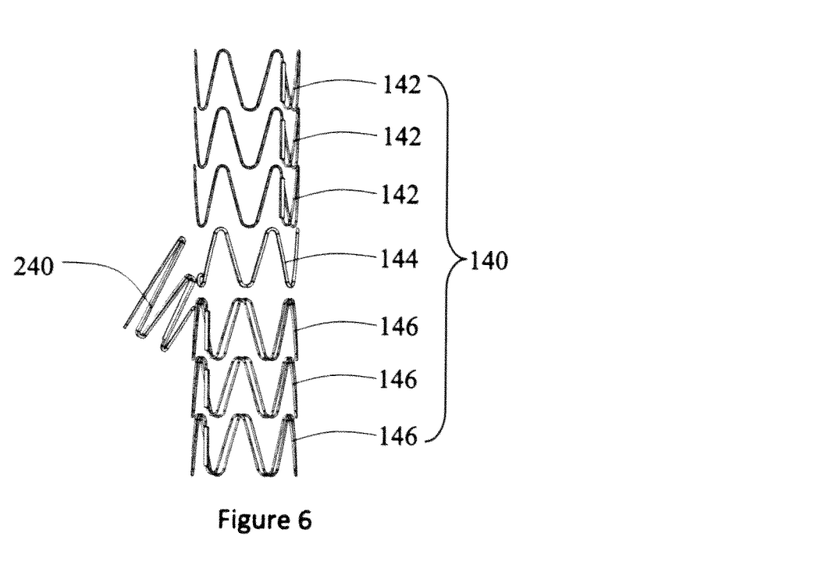
FIG. 6 is a schematic view of a first bare stem of the bifurcated stent graft and a body bare stent of FIG. 4.

Meanwhile, with reference to FIGS. 5 and 6, in one of the embodiments, the body 100 may comprise the body covering film 120 and the body bare stent 140 attached thereon; the body covering film 120 comprises axially the body segment 122, the connecting segment 124 and the long branch segment 126 in sequence; both the body segment 122 and the long branch segment 126 communicate with the connecting segment 124; after the stem 10 is implanted in the vessel, all covering films surround to form a new blood flow channel. Either end of the connecting segment 124 is connected with the body segment 122 and the long branch segment 126 respectively; all three can be integrally formed. The covering film 220 of the side branch 200 communicates with the connecting segment 124; the inner and outer surfaces of the connecting segment 124 are partially cylindrical.

The body bare stem 140 comprises the body metal ring 142 disposed on the body segment 122, the second bare stent 144 disposed on the connecting segment 124 and the long branch metal ring 146 disposed on the long branch segment 126; both the body metal ring 142 and the long branch metal ring 146 can be multi-turn metal rings; the second bare stent 144 can be a single-turn; the multi-turn body metal ring 142, the single-turn second bare stem 144 and the multi-turn long branch metal ring 146 are arranged sequentially. In this embodiment, the first bare stem 240 can be a single-turn metal ring. It is to be noted that the structure of the body 100 is not limiting the scope of this invention, as other configurations are available in other embodiments for the body 100.

Figure 7:
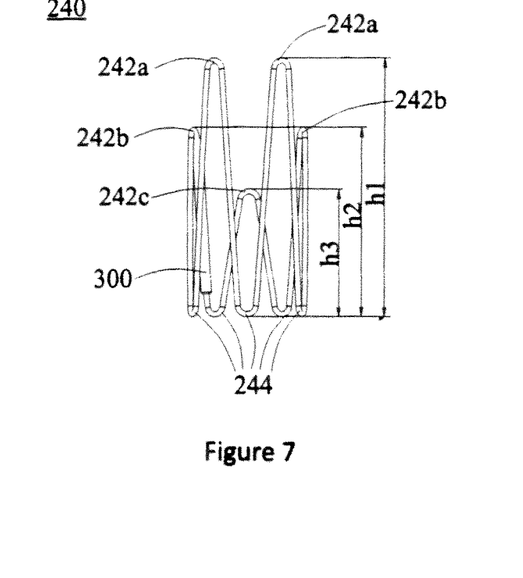
FIG. 7 is a schematic view of a first bare stem of the bifurcated stent graft of FIG. 4.

At the same time, with reference to FIG. 7, a first bare stent 240 comprises a plurality of proximal vertices 242a, 242b and 242c, and a plurality of distal vertices 244, and the proximal vertices are connected with the distal vertices 244 through support parts. The connection lines of the distal vertices 244 are annular (open loop or closed loop), preferably, the connection lines of the distal vertices 244 are positioned along the same circumference, and at least one part of the proximal vertices is positioned in a vertex angle area 250. More preferably, the distal vertices 244 are aligned with the distal end of a covering film 220.

A part of the proximal vertices of the first bare stent 240 is positioned within the vertex angle area 250, such as the proximal vertices 242a and 242b, so that the first bare stent 240 has different waveform heights in the axial length direction of the covering film 220 of a side branch 200, and the waveform heights refer to the axial distances of the proximal vertex and the distal vertex 244. As shown in FIG. 7, according to the position distribution of the proximal vertices relative to the vertex angle area 250, the axial distance h1 of the proximal vertices 242a and the distal vertices 244 is greater than the axial distance h2 of the proximal vertices 242b and the distal vertices 244, and the axial distance h2 of the proximal vertices 242b and the distal vertices 244 is greater than the axial distance h3 of the proximal vertices 242c and the distal vertices 244. According to the differences of the axial lengths of side branch lumen 220, the first bare stem 240 is designed into metal rings with different waveforms, so that other metal rings are not additionally arranged. The first bare stent 240 can be used for sufficiently supporting various parts of the side branch lumen 220, and a second bare stem 144 sufficiently supports a connecting segment 124. Under the sufficient support of the side branch 200 and the connecting segment 124, on one side, a guidewire easily enters the side branch lumen 220. On the other hand, the boundary line 230 and the vertex angle area 250 can be well supported, so that the situation where the covering film 220 is shortened, so that blood vessel channels are narrowed, can be avoided. Meanwhile, the first bare stem 240 and the second bare stent 144 are interdependent, so that the waveform is easily shaped and the technology is simple.

In other embodiments, the second bare stent can also he provided in other structures or waveform structures of other materials, for example, the materials are not provided with elastic rings having swelling capacity, waveform rings made of polymers, and the like. In the embodiment, referring to FIG. 8 and FIG. 9, specifically, the second bare stem 144 is an open loop single-ring waveform, and comprises a terminal end 1442 and a waveform, wherein the waveform comprises a plurality of proximal vertices 1444a and a plurality of distal vertices 1444b; the proximal vertices 1444a and the distal vertices 1444b are connected through the support part. The bare stent 144 is positioned adjacent the boundary line 230, and comprises two end support bars 1446 positioned on two opposite sides of the side branch 200, so as to support the boundary line 230. A waveform segment connected with the terminal end 1442 forms an end support bar 1446, wherein the terminal end 1442 is the tail of the end support bar 1446.

Figure 8:
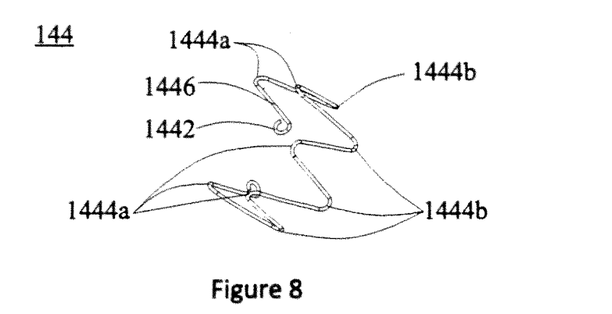
FIG. 8 is a schematic view of a second bare stem of the bifurcated stent graft of FIG. 4.
Figure 9:
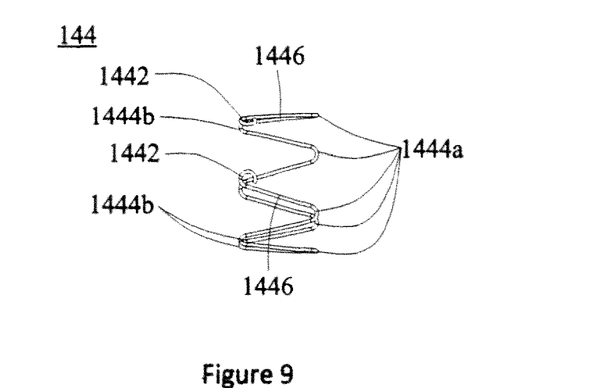
FIG. 9 is a side view of a second bare stem of the bifurcated stem graft of FIG. 4.

Further, two end support bars 1446 of the second bare stent 144 can be mutually parallel and or symmetrical relative to the side branch 200, can be parallel to the axial direction of the second bare stent 144, and can also be non-parallel to the axial direction of the second bare stent 144; of course, one of the end support bars 1446 can also be parallel to the axial direction of the second bare stent 144, and the other be non-parallel to the axial direction of the second bare stent 144. The terminal end 1442 can be fixed to a position adjacent a long branch segment 126 of the connecting segment 124, and can be fixed at the position of a body segment 122; one proximal vertex can be fixed at the position adjacent the long branch segment 126, and the other terminal ends 1442 can be fixed at the position adjacent the body segment 122.

Figure 10:
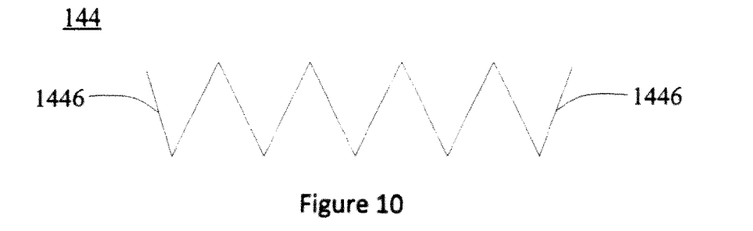
FIG. 10 is a schematic view of a first waveform of the bifurcated stem graft of FIG. 4.
Figure 11:
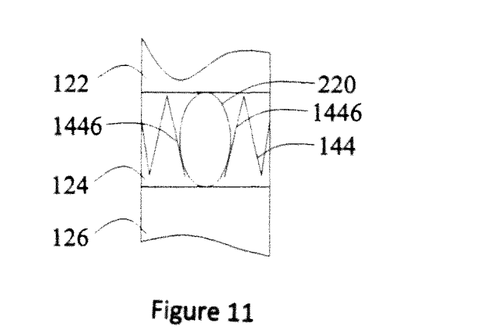
FIG. 11 is a schematic view of the position of a first waveform and covering film of the bifurcated stent graft of FIG. 10.
Figure 12:
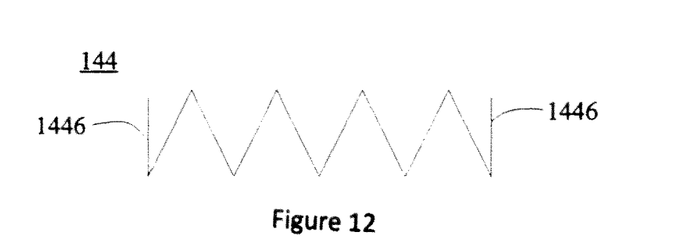
FIG. 12 is a schematic view of a second waveform of the bifurcated stent graft of FIG. 4.

In one embodiment, the waveform of the second bare stem 144 can be a first waveform as shown in FIG. 10 and FIG. 11, and the two end support bars 1446 and the second bare stem 144 are not parallel in the axial direction, and the two end support bars 1446 are mutually non-parallel. The two end support bars 1446 are symmetrical relative to the side branch 200, and the two terminal ends 1442 are fixed at the position adjacent the long branch segment 126 of the connecting segment 124.

Figure 13:
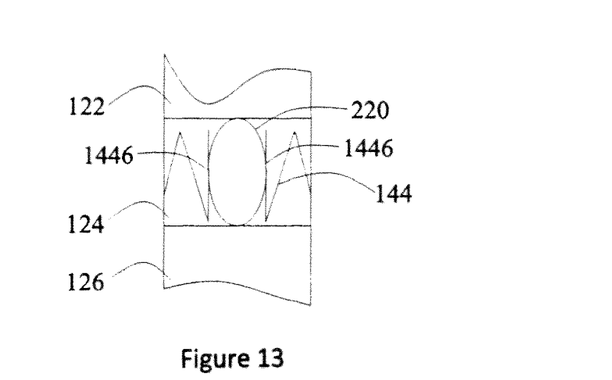
FIG. 13 is a schematic view of the position of a second waveform and covering film of the bifurcated stent graft of FIG. 12.
Figure 14:
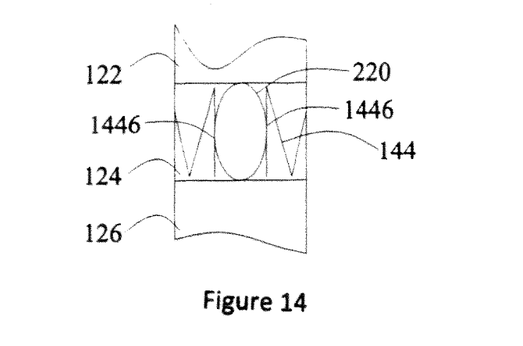
FIG. 14 is another schematic view of the position of a second waveform and covering film of the bifurcated stent graft of FIG. 12.
Figure 15:
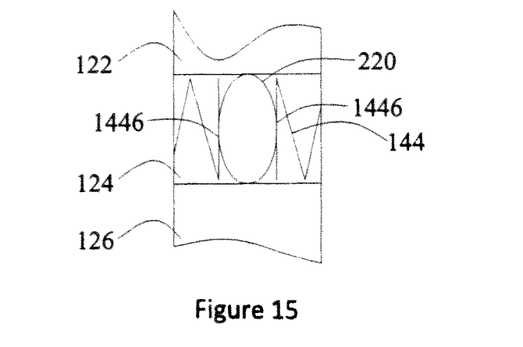
FIG. 15 is still another schematic view of the position of a second waveform and covering film of the bifurcated stem graft of FIG. 12.

The waveform of the second bare stent 144 can also he a second waveform as shown in FIG. 12 to FIG. 15, the two end support bars 1446 and the second bare stent 144 are parallel in the axial direction, the two end support bars are parallel with each other, and the two end support bars 1446 are symmetrical relative to the side branch 200. In the embodiment as shown in FIG. 13, the two terminal ends 1442 are fixed at the position adjacent the body segment 122 of the connecting segment 124. In the embodiment of FIG. 14, the two terminal ends 1442 are fixed at the position adjacent the long branch segment 126 of the connecting segment 124. In the embodiment of FIG. 15, one terminal end 1442 is fixed at the position adjacent the long branch segment 126, and the other terminal end 1442 is fixed at the position adjacent the body segment 122. The end support bars 1446 are parallel to the axial direction of the metal ring, so that the end support bars 1446 on two sides of the opening of the side branch lumen 220 are symmetrical relative to the opening as well as the cross section of the tubular cavity, so that the end support bars 1446 can effectively support the side branch lumen 220, so as to facilitate the entry of the guidewire into the side branch lumen 220.

Figure 16:
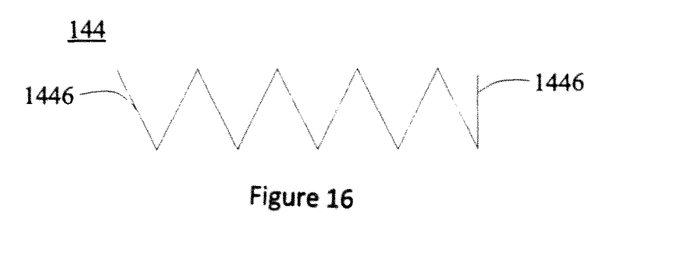
FIG. 16 is a schematic view of a third waveform the bifurcated stent graft of FIG. 4.
Figure 17:
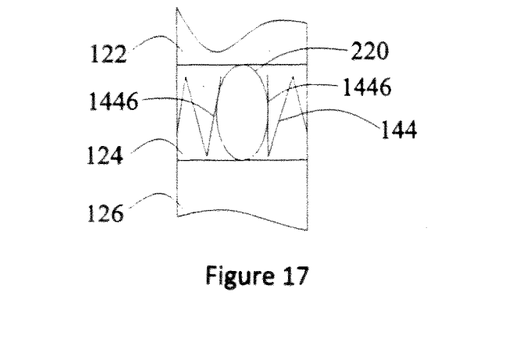
FIG. 17 is a schematic view of the position of a third waveform and covering film of the bifurcated stem graft of FIG. 16.

The waveform of the second bare stent 144 can be a third waveform as shown in FIG. 16 and FIG. 17, wherein one end support bar 1446 is parallel to the axial direction of the second bare stem 144, and the other end support bar 1446 is not parallel to the axial direction of the second bare stent 144. The two end support bars 1446 are not parallel with each other, and the two end support bars 1446 are asymmetric relative to the side branch 200. Compared with the construction shown in FIG. 10 to FIG. 15, the two end support bars 1446 cannot he symmetrical relative to the side branch 200, so that the supporting effect is poor.

Figure 18:
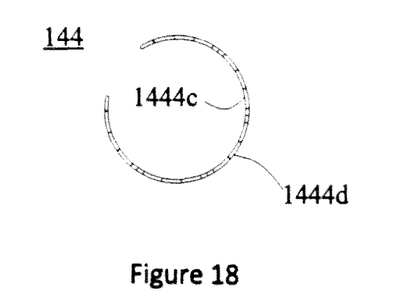
FIG. 18 is a top view of a second bare stent of the bifurcated stent graft of FIG. 4.
Figure 19:
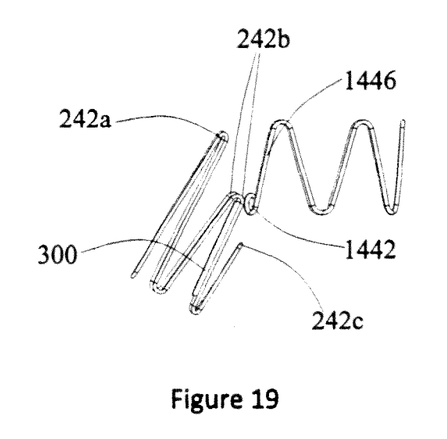
FIG. 19 is a schematic view of a first bare stem and a second bare stent of the bifurcated stent graft of FIG. 4.

Meanwhile, with reference to FIG. 18, the interior surface 1444c of the second bare stent 144 is on one cylindrical surface, the exterior surface 1444d of the second bare stent 144 is on another cylindrical surface, and the interior surface 1444c of the second bare stent 144 and the exterior surface 1444d of the second bare stent 144 both only occupy part of the cylindrical surface. The second bare stent 144 is only fixed on the position of the connection segment 124, and does not extend to the side branch lumen 220; i.e., two terminal ends 1442 both terminate at the junction of the two sides of the body 100 and the side branch 200, and can completely support the connecting segment 124 to form an unobstructed blood flow channel. Meanwhile, with reference to FIG. 19, in the embodiment that the terminal ends are fixed on the position of the connecting segment 124 adjacent the long branch segment 126, the two terminal ends 1442 of the second bare stem 144 can abut on two proximal vertices 242b of the first bare stent 240 respectively.

In order to avoid scratching the blood vessels, sharp parts should not be formed on the second bare stent 144, and the terminal ends 1442 can be designed as a smoothly rounded structure, which can generally he ring shaped, oval shaped, or any curve shaped, and so on. Specifically, the terminal ends 1442 can be generally ring shaped, and in the above-mentioned embodiments, the terminal ends 1442 are ring shaped.

The multi-turn metal rings of the body metal ring 142 and the long branch metal ring 146 both can be a closed independent wave loop, and if there are other metal rings on the stem 10, the other metal rings also can be a closed independent wave loop. Meanwhile, with reference to FIG.

Figure 20:
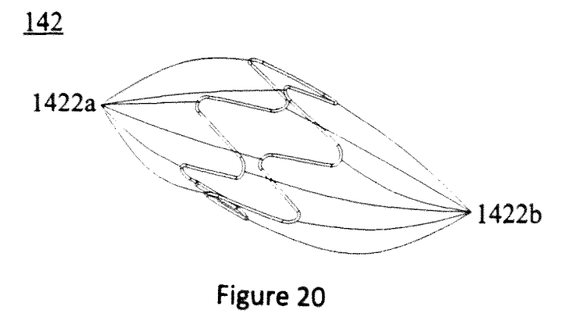
FIG. 20 is a perspective view of a body metal ring of the bifurcated stent graft of FIG. 4.
Figure 21:
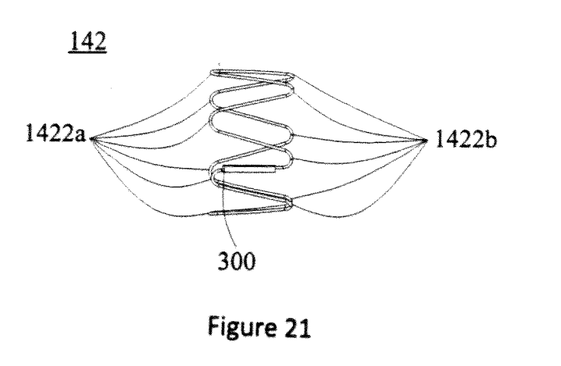
FIG. 21 is a side view of a body metal ring of the bifurcated stent graft of FIG. 4.
Figure 22:
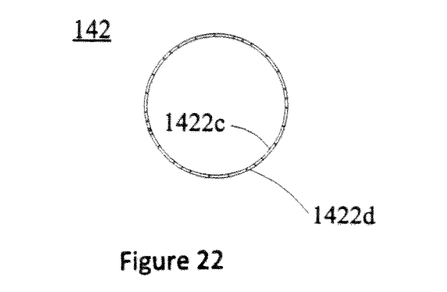
FIG. 22 is a top view of a body metal ring of the bifurcated stent graft of FIG. 4.

20 and FIG. 21, taking the body metal ring 142 for example, the body metal ring 142 includes a plurality of proximal vertices 1442a and a plurality of distal vertices 1442b, wherein the proximal vertices 1442a are connected with the distal vertices 1442b through a support part. Meanwhile, with reference to FIG. 22, the interior surface 1442c of the body metal ring 142 is on one cylindrical surface, and the exterior surface 1442d of the body metal ring 142 is on another cylindrical surface. The multi-turn metal rings of the body metal ring 142 and the long branch metal ring 146 both have the same or a similar shape, for example a Z-shaped wave or other waveforms.

During the fabrication of the above-mentioned first bare stent 240, the body metal ring 142 and the long branch metal ring 146, a metal wire can be woven or cut into a desired waveform, and after the heat setting of the metal wire via a mold, the steel socket 300 as shown in FIG. 7 and FIG. 21 is used as a socket joint to connect both ends of the metal Wire, and the mechanical compression method is used to fixedly connect the metal wire and the steel socket 300, thereby, forming a metal ring. The metal wire can be a nickel-titanium alloy, wire, for example a nickel-titanium alloy wire with the wire diameter of 0.40 mm. After the fabrication of the multi-turn metal rings is completed, surface covering films of the multi-turn metal rings are spaced intermittently and sequentially, and polyethyleneterephthalate (PET) or Polytetranuoroethene (PTFE) can be optionally used as a material for the covering films.

Figure 23:
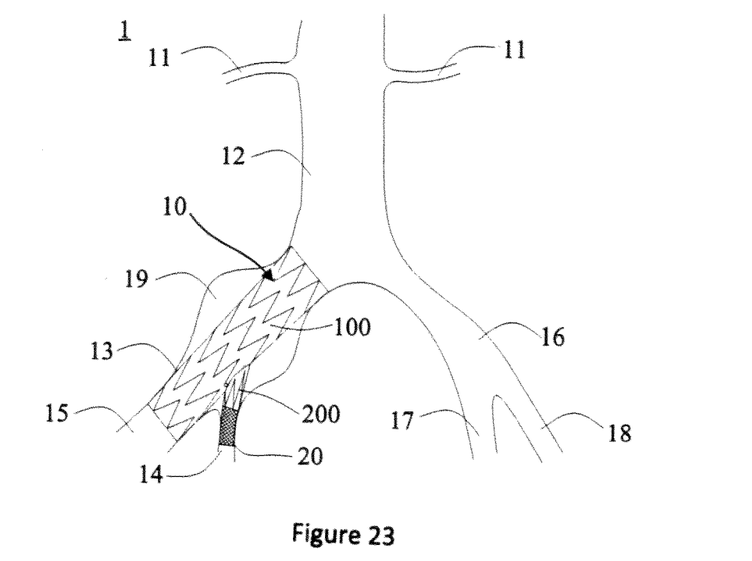
FIG. 23 is an illustration of the bifurcated stent graft implanted into the unilateral isolated iliac communis aneurysm of FIG. 4.
Figure 24:
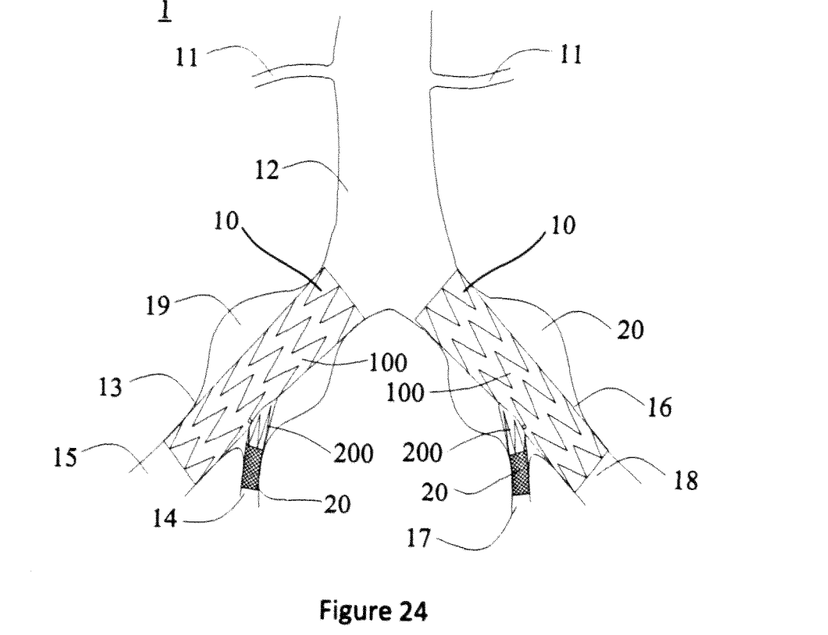
FIG. 24 is an illustration of the bifurcated stent graft implanted into the bilateral isolated iliac communis aneurysm of FIG. 4.
Figure 25:
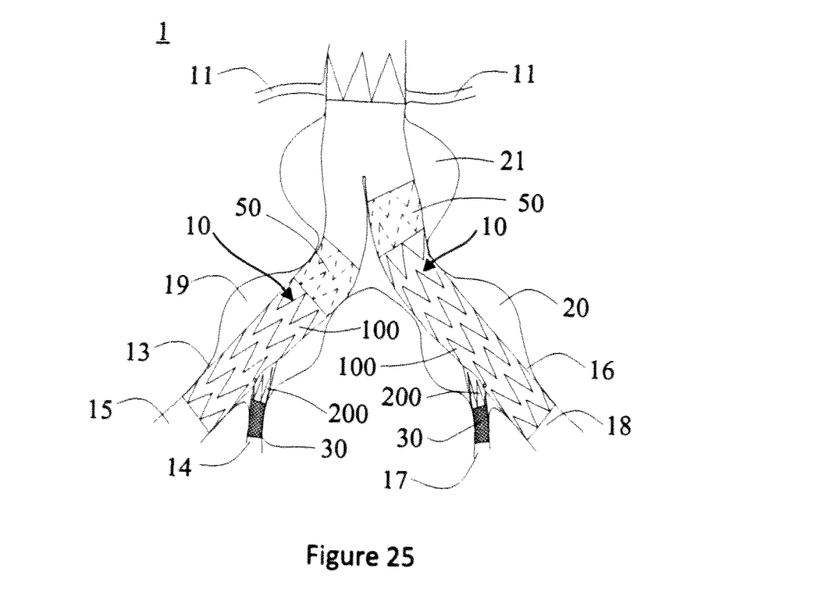
FIG. 25 is an illustration of the bifurcated stent graft combination with an abdominal aortic bifurcated stent graft for the treatment of abdominal iliac aneurysm accompanied with abdominal aortic aneurysm of FIG. 4.

Schematic diagrams of the implantation of the bifurcated stent graft 10 in FIG. 4 being implanted into the abdominal iliac arteries are shown in FIG. 23, FIG. 24 and FIG. 25. A schematic diagram showing how the iliac artery bifurcated stent graft 10 in FIG. 4 combined with the peripheral covering stem 30 opens up the right internal iliac artery is shown in FIG. 23. A schematic diagram showing how the iliac artery bifurcated stent graft 10 in FIG. 4 combined with the peripheral covering stent 30 opens up the bilateral iliac artery is shown in FIG. 24. A schematic diagram showing how the iliac artery bifurcated stem graft 10 in FIG. 4 combined with the peripheral covering stent 30 and abdominal main bifurcated stent graft 50 treats the arteria iliaca communis accompanied with the abdominal aortic aneurysm is shown in FIG. 25. The stent 10 can effectively isolate the blood flow and the artery aneurysm, and the relatively good radial support force of the bifurcation part can maintain the stent 10 continuously in an unobstructed state, thereby guaranteeing that the blood flow is unobstructed in every lumen.

Figure 26:
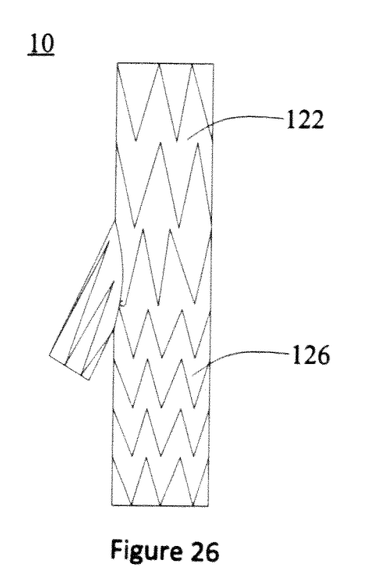
FIG. 26 is a schematic diagram of another embodiment of the bifurcated stent graft.
Figure 27:
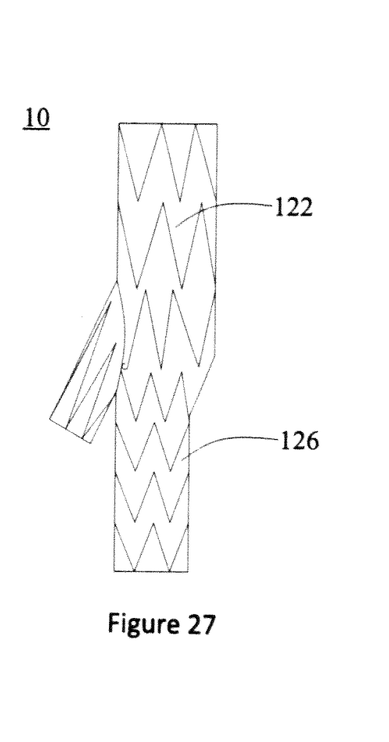
FIG. 27 is a schematic diagram of yet another embodiment of the bifurcated stem graft.

In one embodiment, with reference to FIG. 26, the diameter of the body segment 122 can be as large as that of the lumen of the long branch stem 10. In another embodiment, with reference to FIG. 27, the diameter of the body segment 122 can also be designed to be not as large as that of the long branch segment 126 according to desired requirements, for example, the diameter of the body segment 122 is larger than that of the long branch segment 126.

Figure 28:
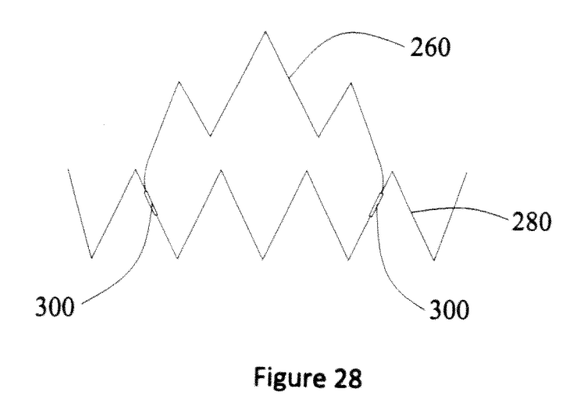
FIG. 28 is a schematic diagram of yet another embodiment of the bifurcated stem graft.
Figure 29:
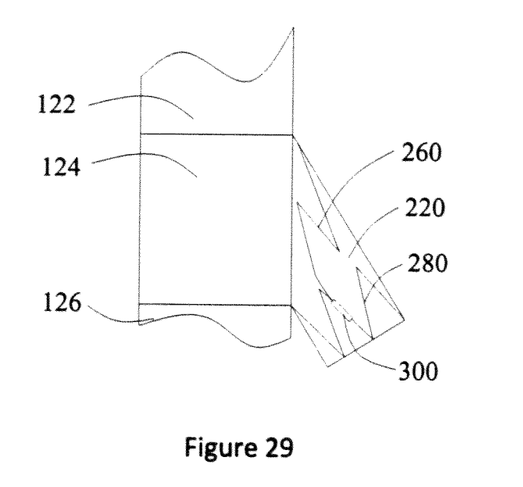
FIG. 29 is a schematic diagram of yet another embodiment of the bifurcated stent graft.

As shown in FIG. 28 and FIG. 29, in another embodiment, the first bare stem 260 can also be structured as a waveform open loop. The side branch 200 also comprises a third bare stent 280 disposed on the covering film 220, and the third bare stent 280 is structured as a waveform close loop and connected with the first bare stent 260. The first bare stent 260 is combined with the third bare stent 280, in order to completely support the side branch 200. Preferably, most or all of the first bare stent 260 is disposed within the top corner region 250 for supporting the top corner region 250, and the second bare stent 280 is used for supporting the other regions of the side branch 200.

In an embodiment, the first bare stem 260 and the second bare stent 280 can be connected and fixed together via the steel socket 300. The first bare stent 260 can be a wave loop with non-equal length waves and or non-equal heights, the distal vertices of the first bare stent 260, i.e. one end proximate to the second bare stem 280 is on the same plane perpendicular to the axis of the side branch 200. The number of the proximal vertices of the first bare stent 260 can be one or more than one; in this example, the number of the proximal vertices of the first bare stent 260 is more than one, and the height of the proximal vertices at the middle position on the plane perpendicular to the axis of the side branch 200 is larger than that of the proximal vertices at either end position. The number of the second bare stent 280 can be one or more than one; in this example, the number of the second bare stent 280 is one, and the second bare stent 280 is a wave loop with average equal length waves and/or non-equal heights. The first bare stent 260 and the second bare stem 280 are both fixed on the side branch lumen 220, and can completely support the side branch lumen 220. The other parts of this embodiment can be the same as those shown in FIG. 4 to FIG. 27.

The above embodiments only express a few embodiments of the present invention, and the description thereof is relatively specific and particular, but these should not thereby be construed as limitations on the scope of the present invention. It should be noted that for those skilled in the art, it will be appreciated that various changes and modifications may be made to the invention as described herein without departing from the spirit and scope thereof, which belongs to the protective scope of the present invention. Therefore, the protective scope of the present invention should only be determined by the appended claims.

The invention claimed is:
1. A bifurcated stent graft, comprising:
a body;
a side branch that forms an acute angle with the body, the side branch comprising a covering film and a first bare stent disposed only on the covering film, with a part of the first bare stent positioned adjacent a boundary line of the body and the covering film, and is located in a vertex angle area of the acute angle; and
wherein the first bare stent comprises at least one metal ring that defines different waveforms that include struts and a plurality of proximal vertices and a plurality of distal vertices, each strut having a proximal vertex and a distal vertex at opposite ends thereof, with an axial distance defined for the strut between each connecting proximal vertex and distal vertex, and wherein the axial distances are different along the at least one metal ring, with the strut closest to the acute angle having the shortest axial distance, and the strut furthest from the acute angle having the longest axial distance.
2. The bifurcated stent graft of claim 1, wherein the plurality of distal vertices defines a connection line, and the connection line of the plurality of distal vertices is annular, with at least a part of the plurality of proximal vertices located in the vertex angle area.
3. The bifurcated stent graft of claim 1, wherein the plurality of distal vertices defines a connection line, and the connection line of the plurality of distal vertices is located along the same circumference, with at least a part of the plurality of proximal vertices located in the vertex angle area.

4. The bifurcated stent graft of claim 3, wherein the covering film has a distal end, and wherein the plurality of distal vertices are aligned with the distal end of the covering film.

5. The bifurcated stent graft according to claim 1, wherein the body comprises a second bare stent positioned adjacent the boundary line and having an axial direction, with the second bare stent comprising two end support bars disposed at the opposite sides of the side branch, wherein one end support bar is parallel to the axial direction of the second bare stent, and the other end support bar is not parallel to the axial direction of the second bare stent.

6. A bifurcated stent graft, comprising:
a body;
a side branch that forms an acute angle with the body, the side branch comprising a covering film and a first bare stent disposed only on the covering film, with a part of the first bare stent positioned adjacent a boundary line of the body and the covering film, and is located in a vertex angle area of the acute angle; and
wherein the first bare stent comprises at least one metal ring that defines different waveforms that include struts and a plurality of proximal vertices and a plurality of distal vertices, each strut having a proximal vertex and a distal vertex at opposite ends thereof, with an axial distance defined for the strut between each connecting proximal vertex and distal vertex, and wherein the axial distances are different along the at least one metal ring, with the strut closest to the acute angle having the shortest axial distance;
wherein the body comprises a second bare stent positioned adjacent the boundary line, with the second bare stent comprising two end support bars disposed at the opposite sides of the side branch, and the two end support bars are parallel to each other or symmetrical relative to the side branch.

7. The bifurcated stent graft of claim 6, wherein each end support bar has a tail, and the tails are smoothly rounded.

8. The bifurcated stent graft according to claim 6, wherein the first bare stent is structured as a waveform open loop, and the side branch also comprises a third bare stent disposed on the covering film, with the third bare stent structured as a waveform closed loop and connected with the first bare stent.

9. The bifurcated stent graft according to claim 6, wherein the strut furthest from the acute angle has the longest axial distance.

10. The bifurcated stent graft of claim 6, wherein the plurality of distal vertices defines a connection line, and the connection line of the plurality of distal vertices is annular, with at least a part of the plurality of proximal vertices located in the vertex angle area.

11. The bifurcated stent graft of claim 6, wherein the plurality of distal vertices defines a connection line, and the connection line of the plurality of distal vertices is located along the same circumference, with at least a part of the plurality of proximal vertices located in the vertex angle area.

12. The bifurcated stent graft of claim 11, wherein the covering film has a distal end, and wherein the plurality of distal vertices are aligned with the distal end of the covering film.

13. The bifurcated stent graft according to claim 6, wherein the body comprises a second bare stent positioned adjacent the boundary line and having an axial direction, with the second bare stent comprising two end support bars disposed at the opposite sides of the side branch, wherein one end support bar is parallel to the axial direction of the second bare stent, and the other end support bar is not parallel to the axial direction of the second bare stent.

14. A bifurcated stent graft, comprising:
a body;
a side branch that forms an acute angle with the body, the side branch comprising a covering film and a first bare stent disposed only on the covering film, with a part of the first bare stent positioned adjacent a boundary line of the body and the covering film, and is located in a vertex angle area of the acute angle; and
wherein the first bare stent comprises at least one metal ring that defines different waveforms that include struts and a plurality of proximal vertices and a plurality of distal vertices, each strut having a proximal vertex and a distal vertex at opposite ends thereof, with an axial distance defined for the strut between each connecting proximal vertex and distal vertex, and wherein the axial distances are different along the at least one metal ring, with the strut closest to the acute angle having the shortest axial distance;
wherein the body comprises a second bare stent positioned adjacent the boundary line and having an axial direction, with the second bare stent comprising two end support bars disposed at the opposite sides of the side branch, and the two end support bars are not parallel to the axial direction of the second bare stent.

15. The bifurcated stent graft of claim 14, wherein the plurality of distal vertices defines a connection line, and the connection line of the plurality of distal vertices is annular, with at least a part of the plurality of proximal vertices located in the vertex angle area.

16. The bifurcated stent graft of claim 14, wherein the plurality of distal vertices defines a connection line, and the connection line of the plurality of distal vertices is located along the same circumference, with at least a part of the plurality of proximal vertices located in the vertex angle area.

17. The bifurcated stent graft of claim 16, wherein the covering film has a distal end, and wherein the plurality of distal vertices are aligned with the distal end of the covering film.

18. The bifurcated stent graft according to claim 14, wherein the body comprises a second bare stent positioned adjacent the boundary line and having an axial direction, with the second bare stent comprising two end support bars disposed at the opposite sides of the side branch, wherein one end support bar is parallel to the axial direction of the second bare stent, and the other end support bar is not parallel to the axial direction of the second bare stent.

19. The bifurcated stent graft according to claim 14, wherein the strut furthest from the acute angle has the longest axial distance.

* * * * *